United States Patent
Manoukian et al.

(10) Patent No.: US 7,811,433 B2
(45) Date of Patent: Oct. 12, 2010

(54) ELECTROCHEMICAL CARBON DIOXIDE SENSOR

(75) Inventors: Mourad Manoukian, Watertown, MA (US); Anthony B. LaConti, Lynnfield, MA (US); Linda A. Tempelman, Lincoln, MA (US); John Forchione, Ashland, MA (US)

(73) Assignee: Giner, Inc., Newton, MA (US)

( * ) Notice: Subject to any disclaimer, the term of this patent is extended or adjusted under 35 U.S.C. 154(b) by 1069 days.

(21) Appl. No.: 11/252,090

(22) Filed: Oct. 17, 2005

(65) Prior Publication Data

US 2006/0096871 A1    May 11, 2006

Related U.S. Application Data

(60) Provisional application No. 60/619,152, filed on Oct. 15, 2004.

(51) Int. Cl.
*G01N 27/40* (2006.01)
(52) U.S. Cl. ............. 204/415; 204/432; 205/792.5; 205/783
(58) Field of Classification Search ......... 204/400–435; 521/27; 205/792.5
See application file for complete search history.

(56) References Cited

U.S. PATENT DOCUMENTS

| 4,882,031 | A  | * | 11/1989 | Furuya ........................ 204/415 |
|-----------|----|---|---------|---------------------------------------|
| 5,518,602 | A  | * | 5/1996  | Kessel ........................ 204/415 |
| 5,527,446 | A  | * | 6/1996  | Kosek et al. .............. 205/792.5 |
| 6,007,697 | A  | * | 12/1999 | Yagi et al. .................... 205/788 |
| 2002/0019448 | A1 | * | 2/2002  | Sugaya et al. ................. 521/27 |
| 2003/0085125 | A1 | * | 5/2003  | Prohaska et al. ............ 204/424 |
| 2004/0129565 | A1 | * | 7/2004  | Prohaska et al. ............ 204/424 |
| 2005/0029124 | A1 | * | 2/2005  | Holmes et al. .............. 205/687 |

OTHER PUBLICATIONS

Ishiji, et al., "Amperometric Carbon Dioxide Gas Sensor Based on Electrode Reduction of Platinum Oxide," *Anal. Chem.*, 65, 2736-39 (1993).
Takahashi, et al., "Handmade Oxygen and Carbon Dioxide Sensors For Monitoring The Photosynthesis Process As Instruction Material For Science Students," *Sensors and Actuators B*, 77, 237-43 (2001).

* cited by examiner

*Primary Examiner*—Nam X Nguyen
*Assistant Examiner*—Gurpreet Kaur
(74) *Attorney, Agent, or Firm*—Wilmer Cutler Pickering Hale and Dorr LLP

(57) ABSTRACT

An electrochemical sensor is provided for the detection of carbon dioxide gas. The sensor includes a non-conductive solid substrate and at least one each of a metal oxide sensing electrode, a reference electrode and a counter electrode positioned on the substrate. A solid polymer electrolyte anion-exchange membrane is in intimate contact with the sensing electrode, reference electrode and counter electrode. The sensor is highly sensitive and selective to carbon dioxide and has very rapid response time.

21 Claims, 8 Drawing Sheets

ELECTROCHEMICAL CARBON DIOXIDE SENSOR

CROSS REFERENCE TO RELATED APPLICATION

This application claims priority from U.S. Provisional Application Ser. No. 60/619,152, filed Oct. 15, 2004.

BACKGROUND

The field relates to a gas sensor and in particular an electrochemical carbon dioxide sensor for applications in the environmental, medical, agricultural, bio-related and food industries including the food packaging and the brewing and carbonated drinks industry.

Carbon dioxide ($CO_2$) is a colorless, odorless and non-combustible gas and is one of the most important gases on the planet. Plants use $CO_2$, people exhale $CO_2$ and $CO_2$ is one of the most plentiful by-products of the combustion process in devices ranging from furnaces to lawn mowers to coal fired electrical power plants. When present in high concentrations in the air (greater than about 70,000 parts per million (ppm)) it acts primarily as a simple asphyxiant without other physiological effects. In indoor environments, it is primarily produced by human metabolism and is exhaled through the lungs.

Monitoring of carbon dioxide emissions from various natural and industrial sources to the environment facilitates a better understanding of the fate of the carbon dioxide in the global carbon cycle, and in indoor environments, monitoring carbon dioxide levels provides for better quality indoor air through feedback control demand ventilation systems.

Monitoring of carbon dioxide levels in patients, in a hospital or clinical setting, is also important because of the central role of carbon dioxide in physiology. Carbon dioxide is a product of the oxidation of energy sources at the cellular level; it is transported in blood and, for the most part, eliminated through the lungs. Thus it is involved in tissue perfusion and metabolism, systemic circulation, lung perfusion and ventilation. It is expected that changes in those basic functions can be indicated or marked by changes in expired $CO_2$, usually expressed as the end tidal partial pressure of $CO_2$ (pet$CO_2$), measured as the plateau section in a capnograph. In addition to end tidal monitoring of carbon dioxide levels in patients, transdermal and sublingual monitoring are alternative methods that provide good correlation with blood carbon dioxide levels.

Furthermore, monitoring of carbon dioxide levels is important in:

A) Agricultural and bio-related process applications: The growth rate and development of plants can be improved by controlling the concentration of carbon dioxide. In greenhouses and mushroom farms, the growth rate and development of mushrooms and plants—from cucumbers to most luxurious roses—can be improved by controlling the concentration of carbon dioxide. This raises the productivity and quality of the crops. Furthermore, measuring and monitoring of dissolved carbon dioxide levels in plant cell culture bioreactors is important for plant physiology research.

B) Food packaging industry: Adding carbon dioxide to food packaging can considerably extend the storage and shelf life of meat, cheese as well as fruits and vegetables. In the meat packaging industry, a high concentration of $CO_2$ in the packaging inhibits bacterial growth and retains the natural color of the meat.

C) Brewing and carbonated drinks industry: Measurement and control of carbon dioxide level is important in these beverage applications.

In addition to the applications listed above, measurement and control of carbon dioxide levels are important wherever dry ice is produced, handled and used (e.g., food freezing, cold storage, cargo ships and dry-ice production facilities).

There is a large number of carbon dioxide detectors on the market today, designed for environmental, medical and food process monitoring applications. The method of infrared technology is predominantly used in all commercially available detectors. An infrared source at the end of a measurement chamber emits light into a gas chamber, where any carbon dioxide gas present absorbs part of the light at its characteristic wavelength. The absorbance is proportional to the concentration of $CO_2$ in the gas sample.

Systems using the infrared technology are relatively large and expensive and suffer from some limitations when certain situations may affect the reliability of the carbon dioxide measurement. The infrared spectrum of $CO_2$ has some similarities to the spectra for both oxygen and nitrous oxide. High concentrations of either or both oxygen or nitrous oxide (a greenhouse gas) may affect the sensor's reading and, therefore, a correction factor should be incorporated into the calibration of any detector used in such setting. Furthermore, controlling the humidity of the sample gas is important for the accuracy of the infrared measurements. For example, some non-dispersive infrared analyzers for environmental applications use two glass cryotraps: one to dry the ambient air samples and the second to dry the reference gases.

Currently there are two alternatives to the infrared technology. The first is a colorimetric chemical indicator which is a qualitative measurement of carbon dioxide that changes color in the presence of $CO_2$. The second is a Severinghaus-type sensor, which is based on a pH sensor, where carbon dioxide penetrates into the electrolyte of the sensor and changes the pH value, which can be measured by potentiometric, amperometric or other methods. However, Severinghaus type sensors are affected by electromagnetic disturbances because of their high impedance and are difficult to assemble and use. Carbon dioxide measurement is indirect (pH) and an inverse logarithmic function of p$CO_2$ (carbon dioxide partial pressure). The measurement requires maintenance of a delicate film of 0.1M $NaHCO_3$ solution between a thin glass membrane and a $CO_2$-permeable Teflon membrane. There are problems with bubble formation, drying of the electrolyte, and dilution by water vapor and it appears to be necessary to calibrate the sensor frequently.

SUMMARY

A solid electrochemical carbon dioxide sensor is provided that: 1) overcomes certain limitations of the commercially available infrared sensors, 2) is quantitative rather than qualitative, and 3) is based on the novel application of reversible electrochemical reactions to detect carbon dioxide.

One aspect provides an electrochemical sensor for the detection of carbon dioxide gas. The sensor includes a non-conductive solid substrate and at least one each of a metal oxide sensing electrode, a reference electrode and a counter electrode positioned on the substrate. A solid polymer electrolyte anion-exchange membrane is in intimate contact with the sensing electrode, reference electrode and counter electrode.

In at least some embodiments, the carbon dioxide sensor utilizes a solid polymer electrolyte anion exchange membrane in the chloride, carbonate, bicarbonate or sulfate ion form. In certain embodiments, a quaternary ammonium ion anion exchange membrane is employed. Non-limiting examples of such membranes include R4030 (RAI Manufacturing Company, NY), AR103-QDP (Ionics, Watertown Mass.) and Selemion AMV (Asahi Glass, Japan). In at least some embodiments, the solid non-conductive substrate includes one or more of the following: inorganic materials including alumina, silica and titania, as well as organic polymers or plastics, including polyesters, polyimides, polysulfones, polyethers, polystyrenes, polyethylenes, polypropylenes, polycarbonates and liquid crystal polymers. In certain embodiments, the sensor is arranged in a planar configuration to selectively detect carbon dioxide gas in environmental, medical and food industry applications.

In at least some embodiments, the sensor utilizes electrochemically reversible metal oxide (e.g., $MO$, $M_2O_3$ or $MO_2$) catalysts for the sensing electrode. Platinum oxide, ruthenium oxide and iridium oxide are among the candidate metal oxides that can be used.

Another aspect provides a novel electrochemical carbon dioxide detection method where the current generated from the electrochemical reduction of some of the sensing electrode metal oxide (e.g., $MO$, $M_2O_3$ or $MO_2$) is proportional to the carbon dioxide concentration.

In certain embodiments, regeneration and reactivation of the sensing electrode catalyst oxide layer is performed by oxidation (e.g., $M_2O_3 + H_2O = 2MO_2 + 2H^+ + 2e^-$), through application of periodic electrical pulses to the sensing electrode (i.e. electrochemically connected to the counter electrode on the same solid polymer electrolyte membrane).

In certain embodiments, regeneration of the counter electrode catalyst to its original form is performed by reduction (e.g., $AgCl + e^- = Ag + Cl^-$), through application of periodic electrical pulses.

In certain embodiments, the solid polymer electrolyte membrane is restored to its original ionic form (e.g., chloride ion) by application of periodic electrical pulses, as described above, to the electrodes and catalyst.

BRIEF DESCRIPTION OF THE DRAWING

The following drawings are presented for the purpose of illustration and are not intended to be limiting.

DETAILED DESCRIPTION

A solid electrochemical sensor is provided that utilizes the reversible electrochemical reduction of the sensing catalyst oxide layer by the protons formed by dissociation of $CO_2$, as described below. A similar reaction scheme is reported in Ishiji, "Amperometric Carbon Dioxide Gas Sensor Based On Electrode Reduction of Platinum Oxide," Anal. Chem., 65, 2736-39 (1993) and Ishiji et al., "Handmade Oxygen and Carbon Dioxide Sensors For Monitoring The Photosynthesis Process As Instruction Material For Science Students," Sensors and Actuators B, 77, 237-43 (2001), the teachings of which are incorporated herein by reference, for the electrochemical reduction of Platinum and Ruthenium oxides by protons in liquid electrolyte media. The sensor described herein can operate without liquid electrolyte (i.e., using only water) due to the use of a solid anion exchange membrane. In certain embodiments, this sensor performs such electrochemical reactions in a controlled potential (potentiostatically controlled) solid-polymer electrolyte gas sensing configuration comprising a solid chloride, carbonate, bicarbonate or sulfate ion conducting and transporting anion exchange membrane solid electrolyte that is in intimate contact with one or more solid Ag/AgCl electrodes. (Alternatively, Ag/AgCl electrodes can be substituted with Pt/air ($O_2$) electrodes). This yields an economical solid electrochemical sensor for $CO_2$ with a very fast response time (<1 minute for 90% response) and the ability to operate unattended over a very wide humidity and temperature range and applicable for carbon dioxide measurements and monitoring in the environmental, medical and food industries.

Figure 1:
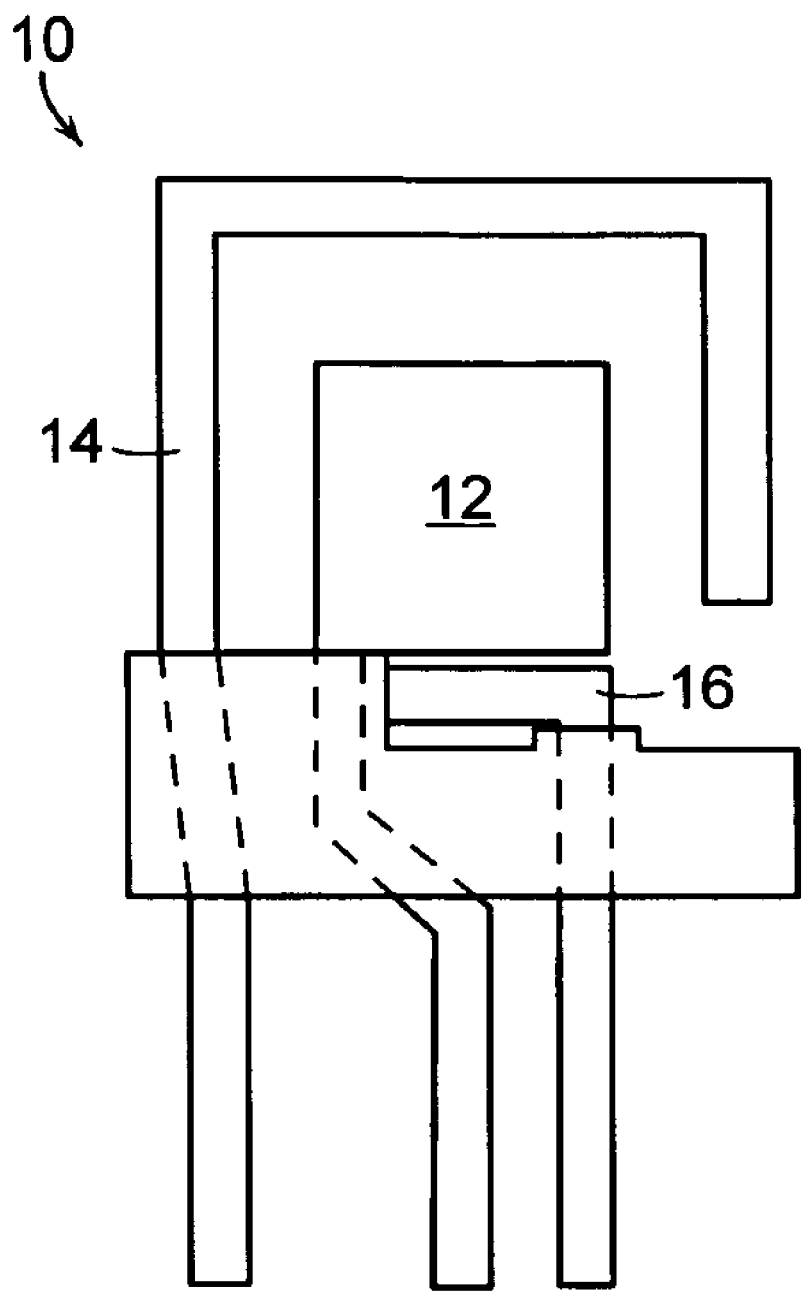
FIG. 1 is a top view of a carbon dioxide sensor according to certain embodiments.
Figure 2:
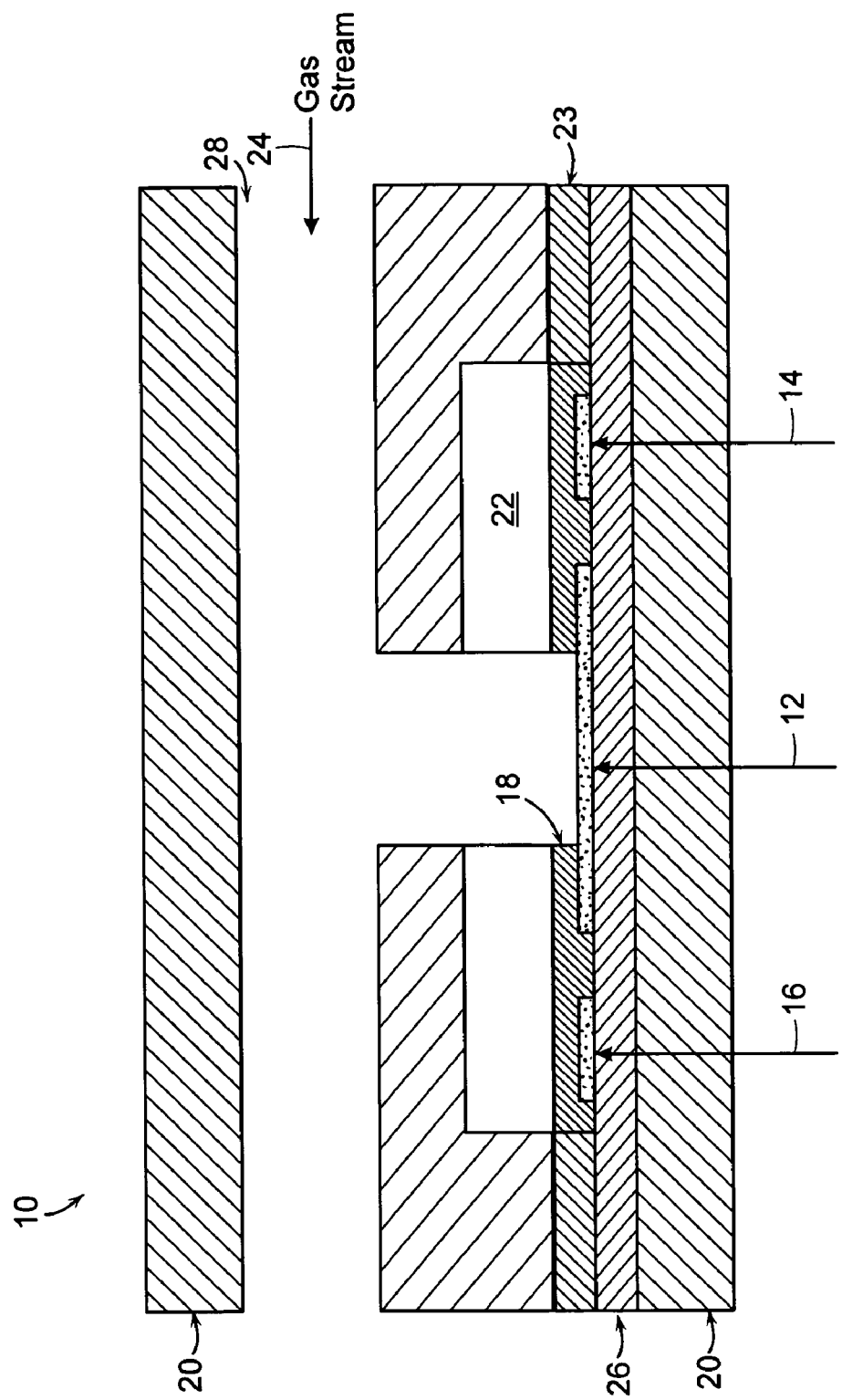
FIG. 2 is a cross-sectional view showing a carbon dioxide sensor assembled in a housing according to certain embodiments.

Referring to FIG. 1, the sensor 10 includes a thin metal oxide ($MO$, $M_2O_3$ or $MO_2$) sensing electrode 12, a silver or platinum counter electrode 14 and silver/silver chloride or Pt/air reference electrodes 16 screen printed or deposited thermally or electrochemically on a non-conductive substrate in a planar, three electrode configuration. The electrodes are all in intimate contact (unitized, bonded) to an anion-exchange solid-polymer electrolyte membrane 18 in its chloride, carbonate, bicarbonate or sulfate ion form, as shown in FIG. 2. In certain embodiments, the membrane is a quaternary ammonium ion anion exchange membrane, such as, for example, R4030 (RAI Manufacturing Company, NY), AR103-QDP (Ionics, Watertown Mass.) or Selemion AMV (Asahi Glass, Japan). Membrane 18 is surrounded by gasket 23.

In certain embodiments, the sensor 10 includes a metal oxide (e.g., Pt, Ru, or Ir oxide or combinations thereof) sensing electrode 12, silver counter electrode 14 and silver/silver chloride reference electrode 16, and anion-exchange solid-polymer electrolyte membrane 18 in its chloride ion form. Using a potentiostatic circuit, a potential of +0.2 V (vs. the silver/silver chloride reference electrode) is applied to the sensing electrode 12. At this potential, no reduction of the metal oxide layer occurs in the absence of protons and the resulting background current is minimal. When $CO_2$ permeates the electrode structure and combines with water at the gas/membrane/electrode interface, to release protons ($H^+$ ions), there is an electrochemical reduction of some of the sensing electrode 12 oxide layer accompanied by a corresponding current proportional to the $CO_2$ concentration. The dissociation of $CO_2$ in water is represented by the following reaction:

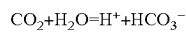

$$CO_2 + H_2O = H^+ + HCO_3^-$$

The $HCO_3^-$ exchanges into the membrane freeing $Cl^-$ ions to react with the silver counter electrode 14 forming AgCl and liberating an electron by the following 2 reactions:

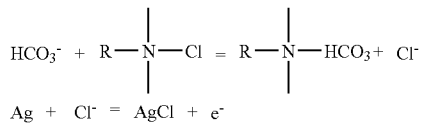

Simultaneously on the sensing electrode 12, some of the metal oxide catalyst (MO, $M_2O_3$ or $MO_2$) material is electrochemically reduced and produces a current proportional to the $CO_2$ concentration. This electrochemically reversible metal oxide reduction is represented by the following chemical reactions:

$$2MO_2 + 2H^+ + 2e^- = M_2O_3 + H_2O$$

or $$MO + 2H^+ + 2e^- = M + H_2O$$

The sensor 10 is periodically charged, by applying electrical pulses, to reactivate and regenerate the $MO_2$ (through oxidation of $M_2O_3$) in the sensing electrode 12 and the counter electrode 14 Ag (through reduction of AgCl). Simultaneously the membrane is restored to the $Cl^-$ ion form as the $Cl^-$ ion is released from the AgCl electrode layer formed during the electrochemical reduction.

Referring to FIG. 2, the sensor 10 including the solid-polymer electrolyte anion-exchange membrane 18 and the non-conductive solid sensor substrate 26 is assembled in a plastic housing 20. The sensor cell housing contains an internal reservoir 22 for water or salt solutions to keep the anion-exchange solid polymer electrolyte hydrated, provides for gas feed 24 to the sensing electrode 12, supports the solid non-conductive sensor substrate 26, provides electrical contact between the electrodes and the electrical circuit and seals the sensor cell 10. In certain embodiments, the reservoir 22 contains only water. Among the various salt solutions that can be used are: potassium chloride (KCl), lithium chloride (LiCl), calcium chloride ($CaCl_2$), sodium carbonate ($NaCO_3$), sodium bicarbonate ($NaHCO_3$), sodium sulfate ($Na_2SO_4$) or corresponding potassium or lithium salt solutions. Use of the water based salts allows operation of the sensor in a wide temperature range (about $-29°$ C. to about $+50°$ C.).

The anion exchange solid-polymer electrolyte 18 membrane is mechanically pressed onto the non-conductive sensor substrate 26 during assembly in the sensor housing 20. The sensor's electrochemically active interface (gas/membrane/electrode interface) is defined by one or more circular, rectangular or other gas diffusion opening or openings in the solid-polymer electrolyte 18 over the sensing electrode 12. Gas inlet port 28 allows gas to enter the sensor housing 20. The gas diffusion path provides free access to the active sensing interface. The sensing electrode 12 is isolated from the counter electrode 14 and reference electrodes 16 to prevent the sample gas from reaching the reference electrode 16, which may change the potential of the reference electrode 16.

The internal water or salt solution reservoir 22 allows continuous hydration of the solid polymer electrolyte 18, but it is isolated from the gas diffusion region to avoid flooding of the sensor electrode 12 active sites. The gas diffusion path, defined by the opening in the sensor cell housing and solid polymer electrolyte (gas chamber), provides diffusion sample gas access to the sensing electrode 12 and the sensor active interfaces. The design and configuration of the gas chamber provides diffusive (not direct) exposure of the sensor active sites to the gas mixture and allows the sensor 10 to operate independent of the flow rate of the gas stream. The gas mix flows into the gas chamber and diffuses down into the gas/membrane/electrode active interface to react.

EXAMPLES

1. $CO_2$ Detection with a Platinum Oxide Sensing Catalyst and Ag Counter and Ag/AgCl Reference Electrodes Platinum oxide was deposited electrochemically on a 6×6-mm screen printed thick-film platinum contact on the sensor substrate (aluminum oxide) by submerging it in 1.5N sulfuric acid solution and applying a potential of 1.30 V vs. normal hydrogen electrode (NHE) for 5 to 10 minutes. Alternatively, the oxide layer was deposited in situ where the sensor substrate was assembled with anion-exchange solid polymer electrolyte membrane in its chloride ion form and the sensing electrode was held at +0.912 V vs. Ag/AgCl reference electrode (1.30 V vs. NHE) for approximately 10 minutes during which time air was passed over the sensing electrode. Silver and silver/silver chloride counter and reference electrodes, as illustrated in FIG. 2, and a quaternary ammonium ion anion exchange membrane (R4030, RAI Manufacturing Company, NY) were used.

Figure 3A:
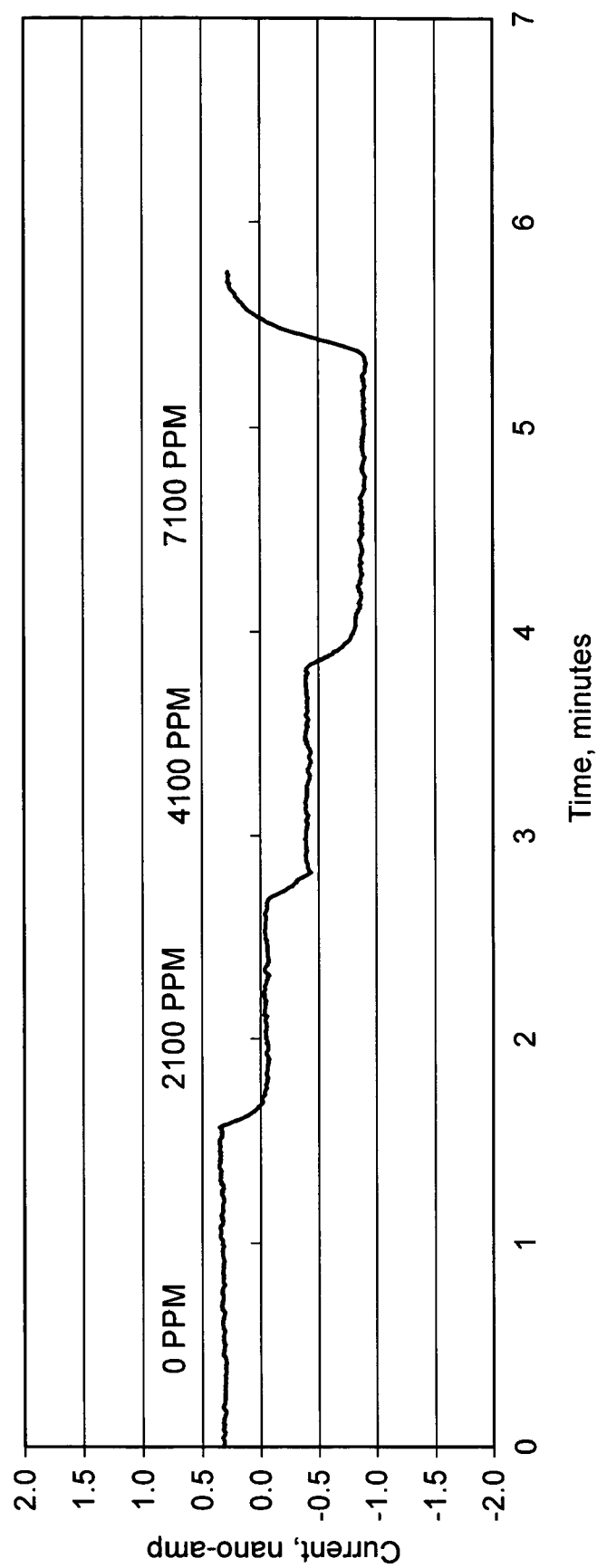
FIGS. 3a-b show response and calibration curves of an anion-exchange membrane platinum oxide sensor according to certain embodiments for carbon dioxide in air mixtures.
Figure 3B:
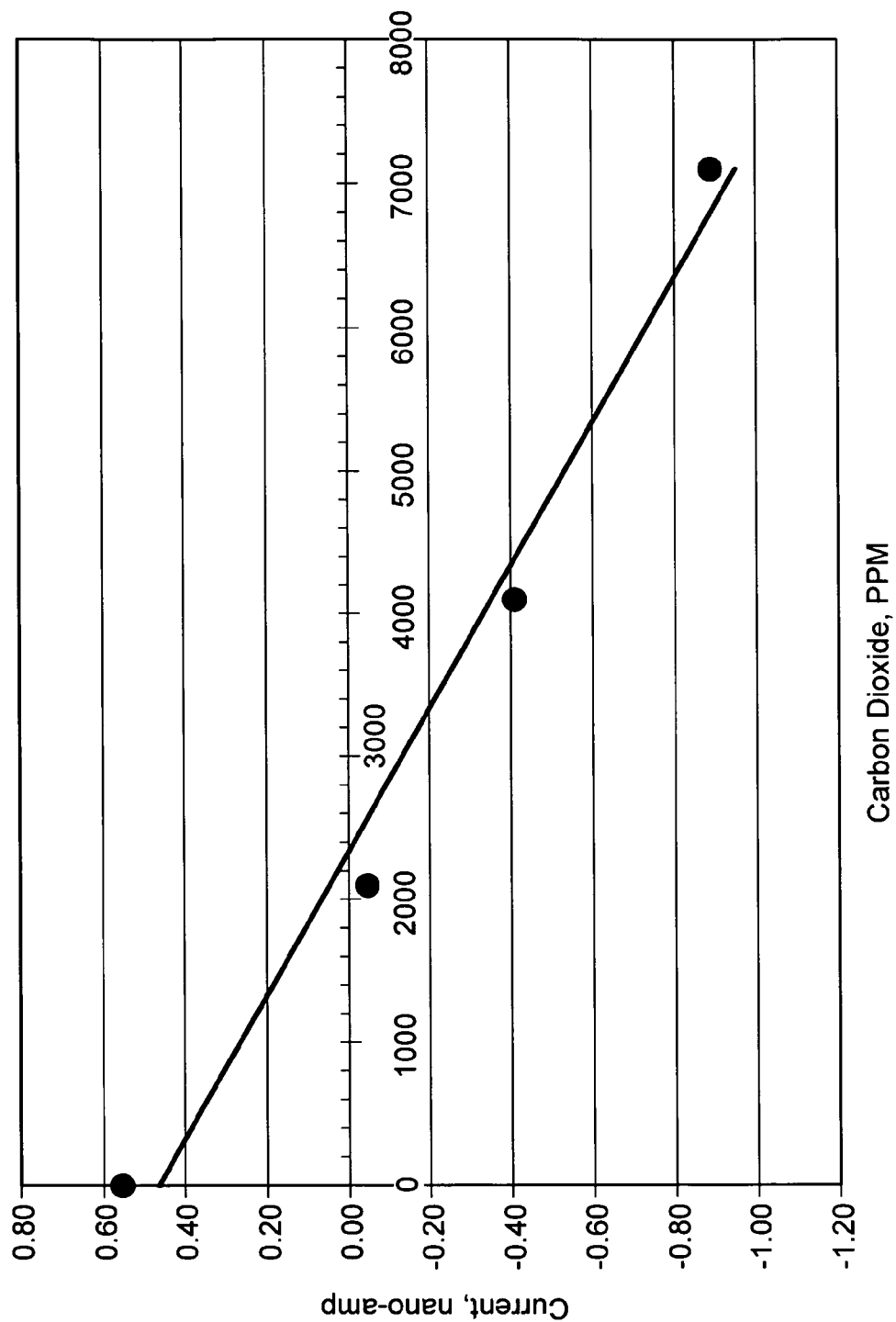

FIGS. 3a and 3b show response and calibration curves of the anion-exchange membrane platinum oxide sensors for carbon dioxide in air mixtures. The concentration of the carbon dioxide was varied incrementally and the response of the sensor was recorded. The sensors were tested in a continuous flow mode where gases from pressurized tanks were mixed with mass flow controllers to achieve the desired concentration and passed over the sensing electrode 12 through the gas inlet port 28 of the sensor cell housing. Current decreased linearly with increasing $CO_2$ concentration.

2. $CO_2$ Detection with a Ruthenium Oxide Sensing Catalyst and Ag Counter and Ag/AgCl Reference Electrodes Ruthenium oxide was deposited on a 6×6-mm screen printed thick-film platinum contact on the sensor substrate (Aluminum oxide) 26 by cyclic voltammetry from an acidic ruthenium chloride solution (5 mM $RuCl_3 \times H_2O$, 0.1M KCl and 0.01M HCl) heated to $50°$ C. The electrode was submerged in the solution and the potential was swept between $-250$ mV to $+950$ mV vs. SCE (Saturated Calomel Electrode, SCE was set up in a separate container and connected to the solution by a capillary bridge) at a rate of 50 mV/second. The counter electrode 14 was a large platinum screen. Ruthenium oxide was deposited by cycling 120 cycles (96 minutes). The sensing electrodes 12 were rinsed with distilled and deionized water, dried in air at $100°$ C. and then heat treated at $145°$ C. in air for 16 hours to stabilize the oxide. The sensor 10 was assembled with a solid-polymer electrolyte anion exchange membrane in its chloride ion form. Silver and silver/silver chloride counter and reference electrodes, as illustrated in FIG. 2, and a quaternary ammonium ion anion exchange membrane (R4030, RAI Manufacturing Company, NY) were used.

Figure 4A:
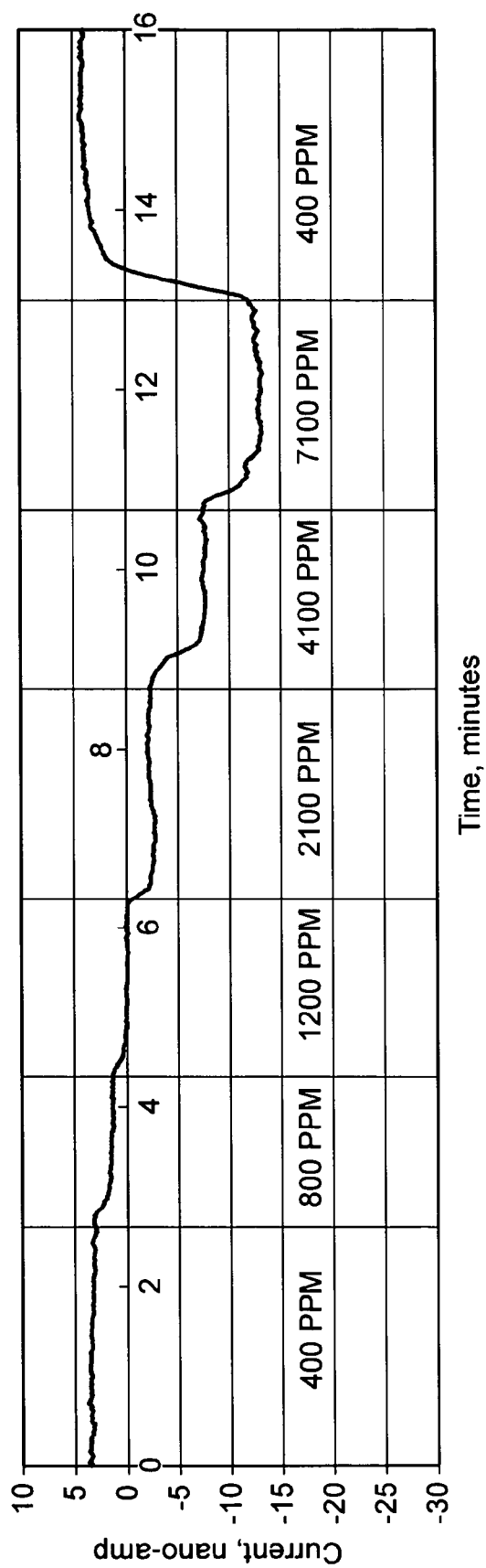
FIGS. 4a-b show response and calibration curves of an anion-exchange membrane Ruthenium oxide sensor according to certain embodiments for carbon dioxide in air mixtures.
Figure 4B:
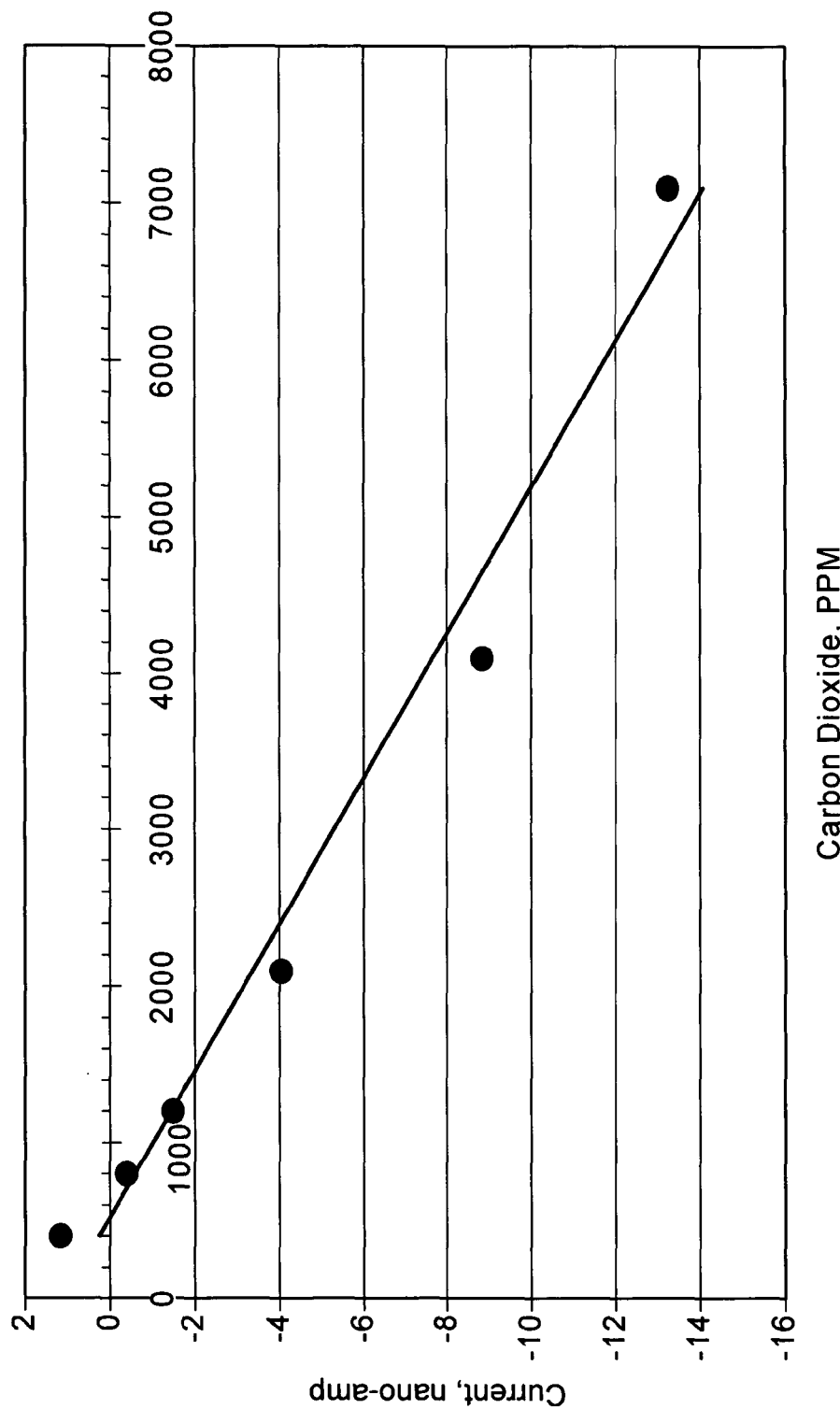

FIGS. 4a and 4b show response and calibration curves of the anion-exchange membrane Ruthenium oxide sensor for carbon dioxide in air mixtures. The concentration of the carbon dioxide was varied incrementally and the response of the sensor was recorded. The sensors were tested in a continuous flow mode where gases from pressurized tanks were mixed with mass flow controllers to achieve the desired concentration and passed over the sensing electrode 12 through the gas inlet port 28 of the sensor cell housing. Current decreased linearly with increasing $CO_2$ concentration.

Figure 5A:
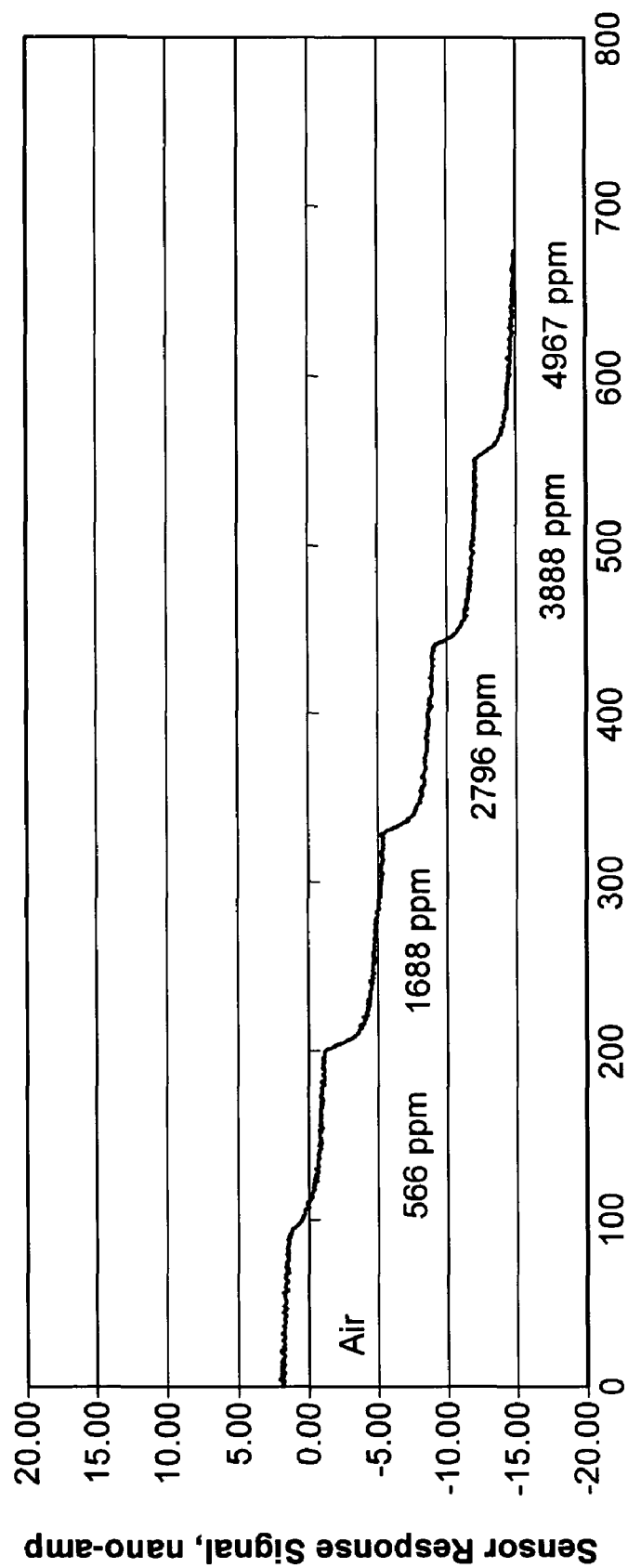
FIGS. 5a-b show response and calibration curves of a thermally deposited thick-film $IrO_2$ sensor according to certain embodiments for carbon dioxide in air mixtures.
Figure 5B:
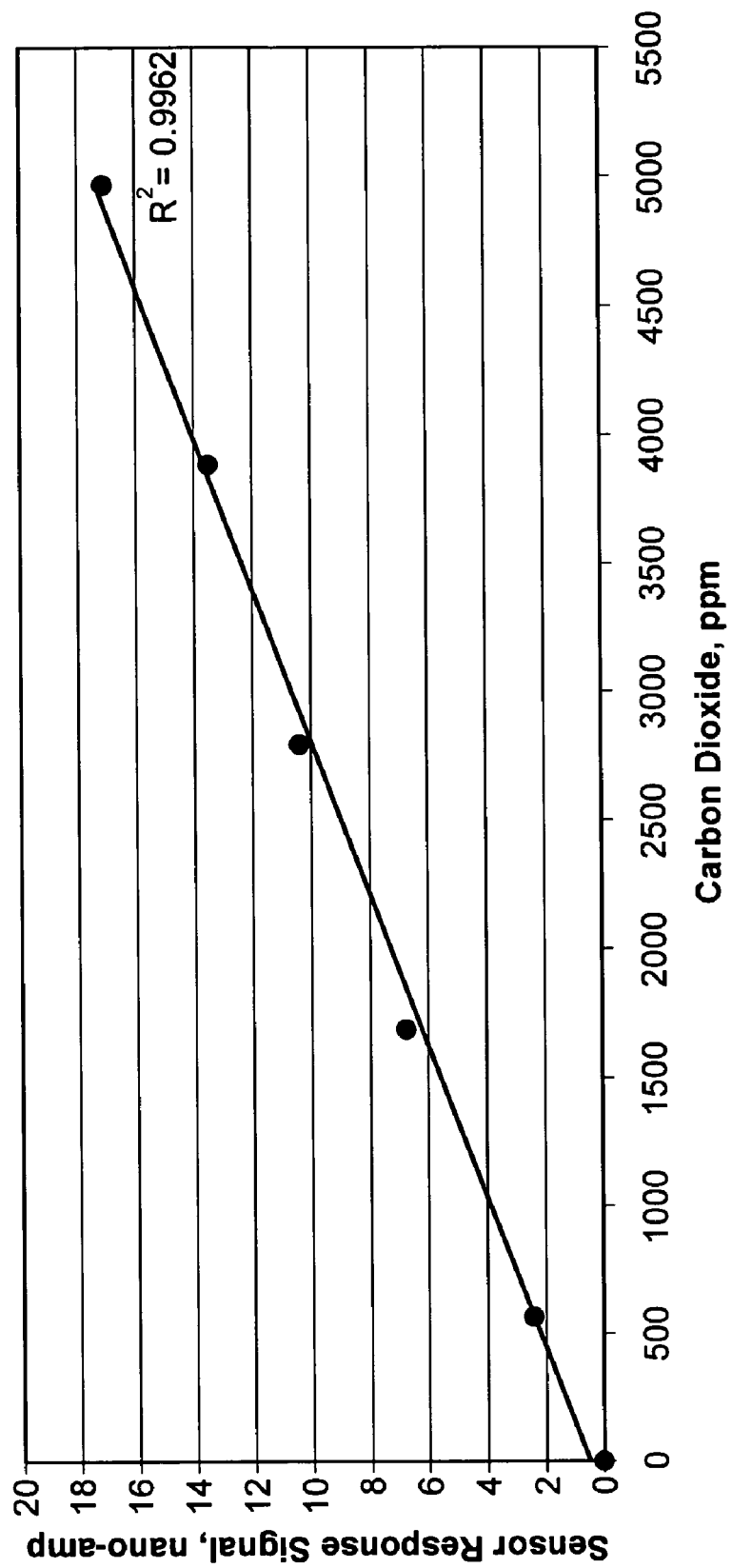

3. CO$_2$ Detection with an Iridium Oxide Sensing Catalyst and Ag Counter and Ag/AgCl Reference Electrodes FIGS. 5a and 5b show response and calibration curves of a thermally deposited thick-film IrO$_2$ sensor for carbon dioxide in air mixtures. Iridium oxide was thermally deposited on a 6×6-mm platinum contact screen printed on a non-conductive substrate (Alumina). Silver and silver/silver chloride counter and reference electrodes, as illustrated in FIG. 2, and a quaternary ammonium ion anion exchange membrane (R4030, RAI Manufacturing Company, NY) were used. The concentration of carbon dioxide was varied incrementally and the response of the sensor was recorded. The sensor was tested in a continuous-flow mode where gases from pressurized tanks were mixed with mass flow controllers to achieve the desired concentration and passed over the sensing electrode 12 through the gas inlet port 28 of the sensor cell housing. Electrical current, resulting from reduction of some of the metal oxide catalyst, decreased linearly to a more negative value with increasing CO$_2$ concentration. Restated, the absolute value of the signal increased linearly with increasing CO$_2$ concentration. The sensor's response time to 90% of its total final response (T$_{90}$) was approximately 45 seconds. This response time includes gas exchange and equilibration time; therefore, the intrinsic response time of the sensor is even faster.

The sensor 10 can be manufactured in a number of different ways. In certain embodiments, the sensor catalyst metal oxide powder is hot pressed onto a supporting and conductive screen substrate. In some embodiments, the reference electrode 16 and counter electrode 14 are hot pressed from powders onto a supporting and conductive screen substrate.

In certain embodiments, the sensing electrode 12 and counter electrode 14 are pressed on one side of a solid polymer anion-exchange membrane with the reference electrode 16 pressed on the opposite side of the anion exchange membrane. Alternatively, the sensing electrode 12 is pressed on one side of a solid polymer electrolyte anion-exchange membrane with the reference electrode 16 and counter electrode 14 pressed on the opposite side of the anion-exchange membrane. In particular embodiments, a Pt/air (O$_2$) electrode is used as a replacement for one or both of the silver containing electrodes (Ag and AgCl).

In certain embodiments, the sensor is operated in a potentiostatic 3-electrode mode, where a constant potential is maintained between the sensing and reference electrodes and the current is measured between the sensing and counter electrodes. In certain embodiments, the sensor can be used in two electrode amperometric mode. In some embodiments, an anion exchange membrane is used in an alternative form other than Cl$^-$ (e.g. carbonate, bicarbonate, sulfate, etc.). In some embodiments, one or more diffusion holes is incorporated in the solid non conducting substrate.

In certain embodiments, the metal oxide catalyst for the sensing electrode 12 is deposited on an inorganic or organic non-conductive substrate (such as alumina, plastics, etc.). In specific embodiments, it is deposited by screen printing from specially formulated screen printable inks; by pressing from powders; by thermal deposition of metal oxide from metal chloride solutions; or by deposition of a thin oxide layer by cyclic voltammetry.

Other alternative embodiments include one or more of the following: the addition of a thin, inert diffusive membrane over the sensor active interface to protect the sensor and to limit water vapor transport; the addition of a thin diffusion film (permselective membrane), covering the sensing electrode 12, to control carbon dioxide diffusion to the sensing electrode 12; the addition of filter plugs to improve selectivity of the sensor, where the filter plug can be filled with activated porous material, such as, e.g., carbon, Purafil (Permanganate on Alumina) and/or platinum; the addition of disposable and replaceable filter plugs to improve selectivity and longevity of sensor 10; the addition of a thin, inert, diffusive and biocompatible membrane over the sensor to protect the sensor in medical applications such as transdermal and sublingual applications; and/or the addition of a disposable and replaceable thin, inert, diffusive and biocompatible membrane over the sensor to increase longevity of sensor.

In certain embodiments, the sensor is configured to be used as a transdermal/transcutaneous carbon dioxide measuring device; a sublingual carbon dioxide measuring device for medical applications; a dissolved carbon dioxide measuring device; or as an inexpensive disposable sensor. In certain embodiments, the sensor is packaged in a hand-held, benchtop, wall-mount, duct-mount and/or in-line device complete with provisions for data display, read-out and storage.

We claim:

1. An electrochemical sensor for the detection of carbon dioxide gas comprising:
    a non-conductive solid substrate;
    a metal oxide sensing electrode, comprising a metal oxide of composition MO$_2$, where M is Ir or Ru, positioned on said substrate, wherein said metal oxide is electrochemically reduced to M$_2$O$_3$ during carbon dioxide detection;
    a reference electrode positioned on said substrate;
    a counter electrode positioned on said substrate;
    a solid polymer electrolyte anion-exchange membrane in intimate contact with said metal oxide sensing electrode, said reference electrode, and said counter electrode,
    wherein the counter electrode is configured to react with ions released from the membrane during carbon dioxide detection and release the same ions for ion exchange into the membrane during electrical regeneration,
    an electrical pulse generator electrically connected to said metal oxide sensing electrode, said reference electrode, and said counter electrode, for periodically generating at least one electrical pulse that simultaneously regenerates the electrochemically reduced metal oxide, the membrane, and counter electrode to their original form.

2. The sensor of claim 1, wherein said non-conductive substrate is a solid inorganic material.

3. The sensor of claim 1, wherein said non-conductive substrate is an organic polymer or plastic.

4. The sensor of claim 1, wherein said reference electrode is a silver/silver chloride electrode.

5. The sensor of claim 1, wherein said counter electrode is a silver electrode.

6. The sensor of claim 1, wherein said counter electrode is a Pt/air (O$_2$) electrode.

7. The sensor of claim 1, wherein said reference electrode is a Pt/air (O$_2$) electrode.

8. The sensor of claim 1, wherein said counter electrode and said reference electrode are Pt/air (O$_2$) electrodes.

9. The sensor of claim 1, wherein the solid polymer electrolyte of the solid polymer electrolyte anion-exchange membrane is the only electrolyte in the sensor.

10. The sensor of claim 1, further comprising a thin diffusion film (permselective membrane) covering said sensing electrode to control carbon dioxide diffusion to the sensing electrode.

11. The sensor of claim 1, wherein said sensing electrode is covered by a disposable and replaceable thin diffusion film.

12. The sensor of claim 1, wherein said solid polymer electrolyte anion-exchange membrane is a quaternary ammonium ion anion-exchange membrane.

13. The sensor of claim 1, wherein said solid polymer electrolyte anion-exchange membrane is in the chloride ($Cl^-$) ion form.

14. The sensor of claim 1, wherein said solid polymer electrolyte anion-exchange membrane is in the carbonate ($CO_3^{2-}$), bicarbonate ($HCO_3^-$) or sulfate ($SO_4^{2-}$) ion form.

15. The sensor of claim 1, wherein said solid polymer electrolyte anion-exchange membrane has one gas diffusion opening in contact with the sensing electrode.

16. The sensor of claim 1, wherein said solid polymer electrolyte anion-exchange membrane has more than one gas diffusion openings in contact with the sensing electrode.

17. The sensor of claim 1, wherein said solid substrate has one or more diffusion holes.

18. The sensor of claim 1, wherein said sensor has planar configuration.

19. The sensor of claim 1, wherein said sensor is electronically controlled by a potentiostatic circuit.

20. The sensor of claim 1, wherein the sensor is operated in a potentiostatic three electrode mode, wherein a constant potential is maintained between the sensing and reference electrodes and current is measured between the sensing and counter electrodes.

21. The sensor of claim 1, wherein said sensor is operated in two electrode amperometric mode.

* * * * *